United States Patent [19]

De Vincentiis

[11] 4,435,591

[45] Mar. 6, 1984

[54] COMPOUND WITH ANALGESIC, ANTIINFLAMMATORY AND ANTIPYRETIC ACTIVITY, AND PHARMACEUTICAL COMPOSITIONS THEREFROM

[75] Inventor: Leonardo De Vincentiis, Rome, Italy

[73] Assignee: Ausonia Farmaceutici s.r.l., Pomezia, Italy

[21] Appl. No.: 390,979

[22] Filed: Jun. 22, 1982

[30] Foreign Application Priority Data

Mar. 10, 1982 [IT] Italy ............................... 20074 A/82

[51] Int. Cl.$^3$ ............................................. C07C 69/76
[52] U.S. Cl. ...................................... 560/73; 560/64; 424/308
[58] Field of Search ..................... 560/64, 73; 424/308

[56] References Cited

FOREIGN PATENT DOCUMENTS 1076591 7/1967 United Kingdom .................. 560/73

*Primary Examiner*—Paul J. Killos
*Attorney, Agent, or Firm*—Bucknam and Archer

[57] ABSTRACT

The compound 2-(4-isobutylphenyl)1-propanol 3,4,5-trimethoxybenzoate is described. The substance is prepared by reacting 3,4,5-trimethoxybenzoic acid chloride with 2 (4-isobutylphenyl)1-propanol; preferably in the presence of an acid acceptor. The compound exhibits valuable analgesic, antiinflammatory and antipyretic properties.

2 Claims, No Drawings

COMPOUND WITH ANALGESIC, ANTIINFLAMMATORY AND ANTIPYRETIC ACTIVITY, AND PHARMACEUTICAL COMPOSITIONS THEREFROM

The present invention relates to compounds having analgesic, antiinflammatory and anti-pyretic activity and more specifically to the compound 2-(4-isobutyl-phenyl)1-propanol 3,4,5-trimethoxybenzoate of formula I:

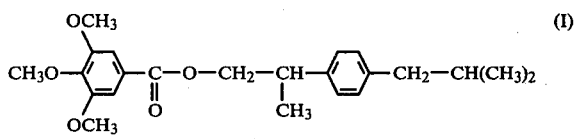

The invention also relates to pharmaceutical compositions having analgesic, antiinflammatory and antipyretic activity containing as the active ingredient the compound of formula I.

The invention also relates to a process for the preparation of the compound of formula I, which consists of reacting 3,4,5-trimethoxybenzoic acid chloride with 2-(4-isobutylphenyl) 1-propanol, preferably in the presence of an acid acceptor, such as pyridine or triethylamine in a solvent such as dimethylformamide, tetrahydrofuran, or acetonitrile at a temperature between 20° C. and about 100° C., preferably at 50°–80° C.

The example hereinbelow illustrates the process according to the invention, but is not intended to limit the scope of the present invention.

EXAMPLE

To a solution of 208 grams, (1.083 moles) of 2,(4-isobutylphenyl)-1-propanol, (Brufenolo), and 250 grams of 3,4,5-trimethoxybenzoyl chloride (1.083 moles) in 1500 cc of dimethyl formamide, there is added dropwise, 87.3 cc (1.083 moles) of pyridine, keeping the temperature at about 60° C. After the addition, the solution is allowed to stand at about 66° C. for five hours, a substantial amount of the solvent is then evaporated under vacuum and the residue is poured into about 800 grams of cracked ice. The precipitate is dissolved in $CH_2Cl_2$, the organic phase is washed with water, dilute HCl and then a saturated aqueous $NaHCO_3$ solution. The material is dried over $MgSO_4$ and the solvent is allowed to evaporate. The residue is recrystallized from isopropanol. There is obtained 180 grams of pure product of melting point 58°–63° C.

Elementary Analysis:

Calculated for $C_{23}H_{30}O_5$ (mol. wt.=386.5): Calculated % C=71.45; H=7.85. Found % C=71.63; H=7.77.

Spectrum $H^1NMR$ (registered in $CDCl_3$, internal reference TMS, the value of the chemical shifts are expressed in δ): 0.9 (d, 6H, ($CH_3$)$_2$CH); 1.3 (d, 3H, Ch$_3$—CH-phenyl); 1.8 (m, 1H, CH(CH$_3$)$_2$); 2.5 (d, 2H, $CH_2$-phenyl); 3.2 (m, 1H, CH-phenyl); 3.9 (s, 9H, 3(CH$_3$O)); 4.4 (d, 2H, CH$_2$—O—CO); 7–7.3 (m, 6H aromatic).

The pharmaco-toxicological properties of the compound of Formula I which will be referred to by the symbol AFP 802 are reported hereinbelow.

Acute Toxicity

The toxicity has been studied by a single administration of AFP 802 in mice and rats using both the oral as well as the intraperitoneal route. As a standard of comparison, there is utilized ibuprofen. The values of $DL_{50}$ have been calculated according to the method of Litchfield and Wilcoxon (J. Pharm. Exp. Therap., 1949, 96, 99). On the basis of the results which are obtained which are summarized in Tables 1 and 2, AFP 802 is a reliable compound with values of $DL_{50}$ more favorable than ibuprofen particularly by the oral route.

TABLE 1

Acute Toxicity by the oral route of AFP 802 and ibuprofen

| Treatment | Animal Species | $DL_{50}$ mg/kg (limit of error 95%) |
|---|---|---|
| AFP 802 | mice | >4,000 |
|  | rats | >4,000 |
| Ibuprofen | mice | 1,433 (1102–1862) |
|  | rats | 975 (793–1199) |

TABLE 2

Acute Toxicity by the intraperitoneal route of AFP 802 and ibuprofen

| Treatment | Animal Species | $DL_{50}$ mg/kg (limit of error 95%) |
|---|---|---|
| AFP 802 | mice | 1,750 (1166–2625) |
|  | rats | 193 (158–235) |
| Ibuprofen | mice | 154 (128–184) |
|  | rats | 185 (145–222) |

Anti-inflammatory Activity

The anti-inflammatory activity has been investigated by a series of tests using edema caused by carrageenan and kaolin pleuritis caused by carrageenan and arthritis caused by an adjuvant.

Edema caused by carrageenan in rats according to the method of Winter et al (Proc. Soc. Exp. Biol. Med., 1962, III, 544). The product under examination and ibuprofen for comparison have been administered in equimolar doses by the oral route 30 minutes prior to the subplantar injection of carrageenan. The plyethysmographic observations of the edema have been carried out every hour for a period of 7 hours after the induction of the edema. The results which are obtained are reported in Table 3.

Edema caused by kaolin in rats according to the method of R. Coulon et al (Arch. Int. Pharmacodyn. 1954, 99, 3): the intra-articular injection of kaolin has been made in the hind paws in rats for determination of the inflammatory reaction which manifests itself with a substantial increase of the articular diameters, inflammatory reaction which continues for several days.

The inhibitory effect of AFP 802 and by comparison also ibuprofen has been studied administering both products in equimolar doses by the oral route, every 24 hours, for a period of 5 consecutive days, beginning one hour after the injection of kaolin. The results which are obtained are expressed in terms of total Area under the curve of the increase of the diameter of the articulations, as shown in Table 4. The results show that AFP 802 inhibits the inflammation to a substantial extent with values which overlap with the values obtained in the case of ibuprofen.

Pleuritis caused by carrageenan in rats. This pleuritis has been investigated according to the method of R.

Vinegar et al (Proc. Soc. Exp. Biol. Med., 1973, 143 3): AFP 802 and ibuprofen are administered by the oral route in equal doses by weight one hour prior to the injection of carrageenan in the pleuritic cavity. The animals are then killed, one half after 5 hours and the other half after 24 hours. By determination of the volume of the pleuric exudate and the total number of leucocytes present in the exudate, it is possible to demonstrate that AFP 802 exerts after 5 hours of the treatment a 43% protection on the volume of the exudate and 72% on the number of the leucocytes.

TABLE 3

Anti-inflammatory Activity - subplantar edema caused by carrageenan in rats

| Treatment | Dose mg/Kg/os | Average volume of the paw after different hours of treatment | | | | | | Area Absolute Value | % inhibition vs control |
|---|---|---|---|---|---|---|---|---|---|
| | | 0 | 1 | 2 | 3 | 4 | 5 | | |
| Controls | — | 22.3 | 29.1 | 35.1 | 40.2 | 42.7 | 41.8 | 300.7 | — |
| AFP 802 | 187 | 22.6 | 27.9 | 28.6 | 28.4 | 28.9 | 29.6 | 119.3 | 60.4 |
| Ibuprofen | 100 | 23.2 | 26.5 | 28.0 | 28.8 | 29.6 | 31.2 | 102.8 | 65.0 |

These values are analogous to the values obtained by administration of equal doses by weight of ibuprofen but it should be stressed that this means that in the case of AFP 802 the quantity of ibuprofen is 1.84 less and, therefore, the pulmonary tropism is substantially more marked for this substance as compared with ibuprofen.

In the test carries out 24 hours after the administration, the effect is more noted because in this case ibuprofen results practically inactive while with AFP 802 the activity which is noted after 5 hours remains practically unchanged. The results are shown in Table 5.

TABLE 4

Antiinflammatory Activity - Edema caused by carrageenan in rats

| Treatment | Dose | No. of Animals | Area mm² | % inhibition with respect to the controls |
|---|---|---|---|---|
| Controls | — | 10 | 17530.5 | — |
| AFP 802 | 115 | 10 | 9799.5 | 44.10 |
| Ibuprofen | 60 | 10 | 10799.5 | 38.24 |

Arthritis caused by the adjuvant in rats was determined according to the method of C. A. Winter and G. W. Nuss (Arthritis and Rheumatism, 1969, 9, 394): AFP 802 and ibuprofen were administered by the oral route in substantially equal amounts for 45 consecutive days, 6 days per week, to rats in which arthritis had been induced by injection of suspension of Micobacterium butirricum.

For the evaluation for the efficiency of the substance the following parameters have been considered: diameter of articulations, volume of the hind paws, hematological and hematochemical examination, weight of the suprarenal glands and thymus. The results which are obtained are summarized in Tables, 6, 7 and 8. On the basis of the results under the experimental conditions used, the high activity of AFP 802 is clear, essentially analogous to that of ibuprofen.

TABLE 5

Anti-inflammatory Activity - Pleuritis caused by carrageenan in rats

| Treatment | Dose mg/Kg/os | Hour | Volume of exudate in cc | % inhibition with respect to the controls | Number of leucocytes × 1,000 | % inhibition with respect to the controls |
|---|---|---|---|---|---|---|
| Controls | — | 5 | 0.99 | — | 17,041 | — |
| | | 24 | 0.92 | — | 18,301 | — |
| AFP 802 | 100 | 5 | 0.56 | 43.43 | 4,804 | 71.80 |
| | | 24 | 0.47 | 48.91 | 7,676 | 58.05 |
| Ibuprofen | 100 | 5 | 0.55 | 44.44 | 4,499 | 73.60 |
| | | 24 | 0.87 | 5.43 | 18,470 | 0.92 |

Analgesic Activity

The analgesic activity of AFP 802 has been studied by means of the writhing test with phenylquinone in mice and by means of the test of Randall and Selitto in rats.

Writhing caused by phenylquinone in mice according to the method of E. Siegmung et al (Proc. Soc. Exp. Biol. Med., 1957, 95, 729): AFP 802 has been administered by the oral route 30 minutes after the injection of phenylquinone and ibuprofen in equal weight has been administered by way of comparison. The results which are obtained, reported in Table 9, demonstrate the equal activity of the two products under examination despite the difference of the molecular weight of the two substances.

Test of Randall and Selitto in rats. This test was carried out according to the method of L. Randall and J. Selitto reported in Arch. Int. Pharmacodyn., 1957 III, 409. AFP 802 and ibuprofen were administered by the oral route in equal doses by weight 30 minutes prior to the subplantar injection of carrageenan in the hind right paw of each animal.

The variations of pressure tolerated without variation in pain have been determined each hour, for 5 consecutive hours and the results are reported in Table 10.

TABLE 6

Anti-inflammatory Activity - Arthritis caused by the adjuvant of Freund in rats. Volume and diameter of both paws (Right = D; Left = S), expressed in area under the curve of the increases

| Treatment | Dose mg/Kg/die os | X̄ Diameter D + S | | X̄ Volume D + S | |
|---|---|---|---|---|---|
| | | Area | % inhibition | Area | % inhibition |
| Control in Blank | — | 1,059.5 | 88.22 | 6,136 | 79.52 |
| Arthritic Controls | — | 8,999.2 | — | 29,965 | — |
| AFP 802 | 100 | 2,602.0 | 71.08 | 15,652 | 47.76 |
| Ibuprofen | 100 | 2,616.2 | 70.92 | 10,335 | 65.5 |

TABLE 7

Anti-inflammatory Activity - Arthritis caused by the adjuvant of Freund in rats Modifications of the seroproteic state

| Treatment | Dose mg/Kg/die os | ALBUMIN (%) | GLOBULIN (%) | | | | |
|---|---|---|---|---|---|---|---|
| | | | α1 | α2 | β1 | β2 | γ |
| Control in Blank | — | 71.4 ± 1.55 | 6.2 ± 0.44 | 5.0 ± 0.26 | 11.3 ± 0.66 | 5.0 ± 0.56 | 2.4 ± 0.19 |
| Arthritic Controls | — | 61.7 ± 2.96 | 11.4 ± 1.58 | 8.0 ± 0.84 | 13.8 ± 0.79 | 6.1 ± 0.43 | 1.9 ± 0.20 |
| AFP 802 | 100 | 70.3 ± 0.97 | 7.2 ± 0.36 | 6.2 ± 0.38 | 11.7 ± 0.30 | 5.7 ± 0.45 | 2.0 ± 0.31 |
| Ibuprofen | 100 | 68.0 ± 2.0 | 8.8 ± 1.07 | 5.5 ± 0.34 | 13.9 ± 0.45 | 5.9 ± 0.43 | 1.9 ± 0.13 |

TABLE 8

Anti-inflammatory Activity - Arthritis caused by the adjuvant of Freund in rats Hematological examination and weight of thymus and suprarenals

| Treatment | Dose mg/Kg/die os | Leucocytes × mm³ | Red Cells × mm³ | Hematocrit | Thymus mg | Suprarenal mg | VES |
|---|---|---|---|---|---|---|---|
| Control in Blank | — | 5,027 ± 406.3 | 5,347.700 ± 1.059 | 47.3 ± 0.1 | 395.0 ± 15.5 | 60.9 ± 2.6 | 0.4 ± 0.1 |
| Arthritic Controls | — | 10,085 ± 579.6 | 5,929.600 ± 1.072 | 46.0 ± 0.9 | 371.8 ± 20.5 | 64.3 ± 2.1 | 12.8 ± 3.61 |
| AFP 802 | 100 | 7.779 ± 385.7 | 5,912.600 ± 1.434 | 46.1 ± 0.6 | 422.3 ± 19.1 | 64.5 ± 3.3 | 0.9 ± 0.1 |
| Ibuprofen | 100 | 7,946 ± 380.5 | 5,265.300 ± 1.003 | 45.4 ± 1.04 | 375.0 ± 24.3 | 65.6 ± 3.4 | 1.7 ± 0.9 |

TABLE 9

Analgesic Activity - Writhing caused by phenylquinone in mice

| Treatment | Dose mg/Kg/os | No. of Contorsions | % inhibition with respect to the control |
|---|---|---|---|
| Controls | — | 21.1 | — |
| AFP 802 | 100 | 4.5 | 78.2 |
| | 200 | 2.3 | 89.1 |
| Ibuprofen | 100 | 4.5 | 78.6 |
| | 200 | 2.8 | 86.7 |

TABLE 10

Analgesic Activity - Test of Randall and Selitto, in rats; Determination of the area of the increase of the pressure tolerated in both paws (I = inflamed; NI = not inflamed)

| Treatment | Dose mg/Kg/os | AREA ABSOLUTE VALUE | | % INHIBITION WITH RESPECT TO THE CONTROL | |
|---|---|---|---|---|---|
| | | I | NI | I | NI |
| Controls | — | −107.36 ± 23.43 | −115.32 ± 20.91 | — | — |
| AFP 802 | 100 | 11.7 ± 22.1 | −61.20 ± 16.39 | 110.89 | 46.93 |
| Ibuprofen | 100 | −58.6 ± 25.25 | −39.95 ± 33.48 | 45.41 | 65.35 |

The activity of AFP 802 expressed in terms of percent of inhibition of the area with respect to the controls, has resulted to be high, superior to the activity of ibuprofen in limbs affected by edema and it is fair, lower than the activity of ibuprofen in a limb in which no injections have been made in the dosage and under the adopted experimental conditions.

Antipyretic Activity

The experiment has been carried out in rats in which the body temperature has been increased by means of yeast by the method according to J. R. Boissier and P. Simon (Therapie, 1962, 17, 1225).

After hyperthermia had been induced, the rats have been treated by the oral route with AFP 802 and by comparison with ibuprofen in equal doses by weight. The thermic variations, noted every hour over a period of 5 hours after the treatment, are reported in Table 11. Under these experimental conditions, AFP 802 demonstrates to possess an antipyretic activity which is only slightly inferior to the activity of an equal dose of ibuprofen. It is, however, necessary to keep in mind the difference in molecular weight between the two substances under examination.

The data reported hereinbelow demonstrates the longer duration of action of AFP 802 as compared with ibuprofen.

Effects of gastric lesion

The effect of AFP 802 and by comparison, of ibuprofen on the gastric mucosa has been investigated by administering the two substances by the oral route in equimolar doses in rats kept fasting for a period of at least 18 hours.

The examination of the mucosa of the animals carried out 7 hours after the treatment, has shown that the product AFP 802 in total contrast with ibuprofen, causes effects of gastric lesion which are almost negligible. (see Table 12).

TABLE 11

| Treatment | Dose mg/Kg os | Basal | 1 Hour | 2 Hours | 3 Hours | 4 Hours | 5 Hours | % inhibition with respect to control |
|---|---|---|---|---|---|---|---|---|
| Control in Blank | — | 37.50 | 37.59 | 37.38 | 37.42 | 37.43 | 37.46 | — |
| Controls with Hyperthermia | — | 38.40 | 38.40 | 38.24 | 38.19 | 38.09 | 38.18 | — |
| AFP 802 | 100 | 38.73 | 38.22 | 37.75 | 37.51 | 37.16 | 37.04 | 86.12 |
| Ibuprofen | 100 | 38.34 | 37.71 | 37.43 | 37.36 | 36.87 | 37.12 | 121.24 |

Antipyretic Activity - Hyperthermia caused by yeast. Rectal temperature (°C.) at different hours after treatment

TABLE 12

Gastric lesion activity - the determination of the total length of the ulcers and the percent of animals which present the ulcers

| Treatment | Dose mg/kg/os | Average length in mm of ulcers | % of animals with ulcers |
|---|---|---|---|
| Controls | — | 0 | 0 |
| AFP 802 | 187 | 0.2 | 10 |
| Ibuprofen | 100 | 5.4 | 80 |

Pharmacokinetics

AFP 802 has been administered orally in the dose of 200 mg/kg in rats. Ibuprofen is administered to a second group of animals orally in a dose of 100 mg/kg which is the same molar amount with respect to the administration of AFP 802. The animals are killed in groups of four after the following time periods; 15 minutes, 30 minutes, 1 hour, 2 hours, 4 hours, 6 hours and 24 hours. The substances AFP 802 and ibuprofen are analyzed quantitatively in the plasma of the rats.

The determination of the serum composition by the gascromatographic route of AFP 802 demonstrates its presence already after a short period of time in the blood fluid, that is 15 minutes and 30 minutes after the administration, a fact which demonstrates the readily bioavailability by the oral route.

The substance AFP 802 is found in the blood even after the first hour which is the time when ibuprofen, which is its active metabolite, begins to appear. The plasma levels of ibuprofen measured in consecutive periods of time result substantially latent with respect to ibuprofen in equimolar doses. The area under the curve of the plasma levels of ibuprofen (AUC) results substantially similar in the administration of the two substances.

The comparison of the ratio of the organ to the plasma for the concentrations of ibuprofen in the case of the administration of AFP 802 results higher in the case of liver, lungs and uterus and lower in the case of kidney with respect to the values observed after administration of ibuprofen.

The present invention relates also to all the industrial applications involving the use of AFP 802 as a pharmaceutical compound having analgesic, antiinflammatory and antipyretic activity. Therefore, an object of the present invention is to provide a pharmaceutical composition which contain a predetermined amount of AFP 802. The substance according to the present invention may be administered by the oral route, for instance in the form of compresses, capsules, small envelopes containing a granulate or by the rectal route. By way of example the following formulations may be mentioned:

(A) compresses containing 500 mg of AFP 802 with excipients and dispersing agents commonly used in the pharmaceutical industry, to be ingested 1-2 times a day;

(B) capsules of 500 mg of AFP 802 to be ingested 1-2 times a day;

(C) envelopes containing 5 grams of granulate containing sugar and armoa, containing 10-20% of AFP 802 to be ingested 1-2 times a day;

(D) suppositories containing 600 mg of AFP 802 to be taken twice a day.

What is claimed is:

1. The compound 2-(4-isobutylphenyl)1-propanol 3,4,5-trimethoxybenzoate of formula I:

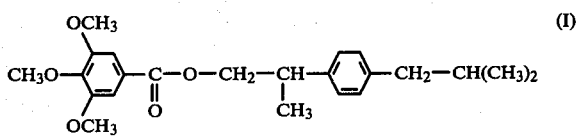

2. A pharmaceutical composition which comprises as the active ingredient 2-(4-isobutylphenyl)1-propanol 3,4,5-trimethoxybenzoate and at least one inert excipient.

* * * * *